United States Patent [19]

Tanzawa et al.

[11] 4,323,648

[45] Apr. 6, 1982

[54] PREPARATION OF MONACOLIN K

[75] Inventors: Kazuhiko Tanzawa; Seigo Iwado; Yoshio Tsujita; Masao Kuroda; Kouhei Furuya, all of Hiromachi, Japan

[73] Assignee: Sankyo Company Limited, Tokyo, Japan

[21] Appl. No.: 137,821

[22] Filed: Apr. 4, 1980

[30] Foreign Application Priority Data

May 11, 1979 [JP] Japan .................................. 54-57927

[51] Int. Cl.³ ............................................ C12P 17/06
[52] U.S. Cl. .................................. 435/125; 435/911; 260/343.5; 424/279
[58] Field of Search .......................................... 435/125

[56] References Cited
PUBLICATIONS

Journal of the Chemical Society (London), pp. 4579–4584, (1961).
Tetrahedron Letters No. 5, pp. 24–27, (1960).

Primary Examiner—Alvin E. Tanenholtz
Attorney, Agent, or Firm—Frishauf, Holtz, Goodman & Woodward

[57] ABSTRACT

Monacolin K, which is an antihypercholesteraemic agent of molecular formula $C_{24}H_{36}O_5$, is prepared by cultivating one or more of the microorganisms *Monascus anka* SANK 10171 (IFO 6540), *Monascus purpureus* SANK 10271 (IFO 4513), *Monascus ruber* SANK 10671 (FERM 4958), *Monascus vitreus* SANK 10960 (FERM 4960), *Monascus paxii* SANK 11172 (IFO 8201), *Monascus ruber* SANK 13778 (FERM 4959), *Monascus ruber* SANK 15177 (FERM 4956) or *Monascus ruber* SANK 18174 (FERM 4957) in a suitable culture medium and then isolating the Monacolin K from the resulting culture broth.

12 Claims, No Drawings

PREPARATION OF MONACOLIN K

BACKGROUND TO THE INVENTION

The present invention relates to a process for preparing an antihypercholesteraemic agent which we have named Monacolin K by cultivating certain specified microorganisms of the genus Monascus.

Monacolin K, which has the formula:

forms the subject of co-pending Application No. 121,515 to the same assignees and has been found to have particularly valuable antihyperlipaemic, especially antihypercholesteraemic, activity.

High blood cholesterol levels are recognized as being one of the main causes of cardiopathy, such as cardiac infarction or arteriosclerosis. As a result, considerable research has been undertaken with a view to discovering physiologically acceptable substances which are capable of inhibiting cholesterol biosynthesis and thus reducing blood cholesterol levels. One such compound is Monacolin K, which forms the subject of said co-pending Application Ser. No. 121,515 filed Feb. 14, 1980, and which can be produced by cultivating microorganisms of the genus Monascus, especially *Monascus ruber* strain 1005 (FERM 4822).

BRIEF SUMMARY OF INVENTION

It is an object of the invention to provide a process for preparing Monacolin K using alternative strains of the genus Monascus.

It is a further object of the invention to provide a biologically pure culture of certain novel strains of the genus Monascus.

Thus, the present invention consists in a process for preparing Monacolin K which comprises cultivating one or more of the mocrooorganisms *Monascus anka* SANK 10171 (IFO 6540), *Monascus purpureus* SANK 10271 (IFO 4513), *Monascus ruber* SANK 10671 (FERM 4958), *Monascus vitreus* SANK 10960 (FERM 4960), *Monascus paxii* SANK 11172 (IFO 8201), *Monascus ruber* SANK 13778 (FERM 4959), *Monascus ruber* SANK 15177 (FERM 4956) or *Monascus ruber* SANK 18174 (FERM 4957) in a culture medium therefor and extracting the Monacolin K from the resulting culture medium.

DETAILED DESCRIPTION OF INVENTION

*Monascus ruber* SANK 10671, *Monascus ruber* SANK 13778, *Monascus ruber* SANK 15177 and *Monascus ruber* SANK 18174 are all newly isolated microorganisms and are described below. The remaining microorganisms are known and have previously been described. All are readily available from IFO or FERM (The Fermentation Research Institute, Agency of Industrial Science and Technology, Ministry of International Trade and Industry, Japan), as indicated by the accession numbers given in parentheses.

The microbiological properties of the new microorganisms are as follows:

*Monascus ruber* SANK 15177 (FERM 4956)

This strain was isolated from soil at Tukimino, Yamato-city, Kanagawa-prefecture, Japan and was deposited on Apr. 27, 1979 under the accession No. 4956 with the said Fermentation Research Institute.

The strain grows well on a potato-glucose-agar medium at 25° C. and produces a soluble colouring material having a yellowish-brown to reddish-brown colour in the medium. It forms any cleistothecia on the basal layer of hyphae.

On oatmeal agar medium, it produces a pale brown colouring material and grows well. Formation of cleistothecia is good and the cleistothecia are spherical, of diameter 30–60 microns and formed on short stalks. These stalks are nearly colourless and branched and of size 25–60×3.5–5.0 microns. The asci are evanescent and thus difficult to observe. The ascospores are colourless and ellipsoid and their dimensions are 4.5–6.5×4.0–5.0 microns; their surfaces are smooth. The conidia are linked basipetally and are of size 7.0–10.0×6.0–10.0 microns.

Although the strain will grow at 37° C., best growth is observed between 23 and 30° C.

*Monascus Ruber* SANK 10671 (FERM 4958)

This strain was isolated from soil at Shinagawa-ku, Tokyo, Japan and was deposited on Apr. 27, 1979 with the said Fermentation Research Institute under the accession No. 4958.

Growth on potato-glucose-agar and oatmeal agar media is similar to that of strain SANK 15177, except that the soluble colouring matter produced is dark red. The diameter of the cleistothecia is 30–80 microns and the dimensions of the stalks are 30–70×3.0–5.0 microns. Asci are not observed. The ascospores are colourless and ellipsoid and their dimensions are 4.5–6.5×4.0–5.0 microns. The conidia are colourless and pyriform or ovoid and their dimensions are 6.0–10.0×6.0–8.5 microns.

*Monascus ruber* SANK 13778 (FERM 4959)

This strain was isolated from soil at Inawashirocho, Nagata, Yama-gun, Fukushima-prefecture, Japan and was deposited on Apr. 27, 1979 under the accession No. 4959 with the said Fermentation Research Institute.

Growth on potato-glucose-agar and oatmeal agar media is similar to that of strain SANK 15177, except that the soluble colouring material produced is a pale reddish-brown to reddish-brown colour. The cleistothecia are of diameter 35–75 microns and the stalks are 30–70×3.5–5.0 microns. Asci are not observed. The ascospores are colourless and ellipsoid and their dimensions are 4.5–6.0×4.0–5.0 microns; their surfaces are smooth. The dimensions of the conidia are 7.0–10.0×6.0–10.0 microns.

*Monascus ruber* SANK 18174 (FERM 4957)

This strain was isolated from soil at Shakotancho, Shakotan-gun, Shiribeshi Shicho, Kokkaido-prefecture, Japan and was deposited on Apr. 27, 1979 with the said Fermentation Research Institute under the accession No. 4957.

Growth on potato-glucose-agar and oatmeal agar media is similar to that of strain SANK 15177, except that the colouring material produced is pale pink. The cleistothecia are of diameter 20–70 microns and the dimensions of the stalks are 20–60×3.0–5.0 microns. Asci are not observed. The ascospores are colourless and ellipsoid and their dimensions are 5.0–7.0×4.0–5.5 microns; their surfaces are smooth. The conidia are linked together basipetally and are colourless and most of them are pyriform and of dimensons 6.0–9.5×6.0–10.0 microns.

Based on the observations of their characteristics as reported above, these microorganisms were all identified as strains of *Monascus ruber* van Tieghem.

Microbiological properties of *Monascus ruber* have been reported in the following literature: Takada, Transactions of the Micological Society of Japn, 9, 125–130 (1969) [Materials for the Fungus Flora of Japan (7)] and van Tieghem, Bull. Soc. Botan. France, 31, 227 (1884). Imperfect state of the strain has been reported by Cole et al in the Canadian Journal of Botany, 46, 987 (1968), "Conidium ontogeny in hyphomycetes. The imperfect state of *Monascus ruber* and its meristem arthrospores".

Monacolin K may be produced by cultivating the chosen microorganism in a culture broth under aerobic conditions using the same techniques as are well-known in the art for the cultivation of fungi and other microorganisms. For example, the chosen strain of Monascus may first be cultivated on a suitable medium and then the produced microorganisms may be collected and inoculated into and cultivated on another culture medium to produce the desired Monacolin K; the culture medium used for the multiplication of the microorganism and the culture medium used for production of Monocolin K may be the same or different.

Any culture medium well-known in the art for the cultivation of fungi may be employed, provided that it contains, as is well-known, the necessary nutrient materials, especially an assimilable carbon source and an assimilable nitrogen source. Examples of suitable sources of assimilable carbons are glucose, maltose, dextrin, starch, lactose, sucrose and glycerine. Of these sources, glucose, glycerine and starch are particularly preferred for the production of Monacolin K. Examples of suitable sources of assimilable nitrogen are peptone, meat extract, yeast, yeast extract, soybean meal, peanut meal, corn steep liquor, rice bran and inorganic nitrogen sources. Of these nitrogen sources, peptone is particularly preferred. When producing Monacolin K, an inorganic salt and/or a metal salt may, if necessary, be added to the culture medium. Furthermore, if necessary, a minor amount of a heavy metal may also be added.

The microorganism is preferably cultivated under aerobic conditions using cultivation methods well-known in the art, for example solid culture, shaken culture or culture under aeration and agitation. The microorganism will grow over a wide temperature range, e.g. from 7 to 40° C., but, especially for the production of Monacolin K, the more preferred cultivation temperature is within the range from 20 to 30° C.

During the cultivation of the microorganism, the production of Monacolin K may be monitored by sampling the culture medium and measuring the physiological activity of the Monacolin K in the culture medium by the tests described hereafter. Cultivation may then be continued until a substantial accumulation of Monacolin K has been achieved in the culture medium, at which time the Monacolin K may then be isolated and recovered from the culture medium and the tissues of the microorganism by any suitable combination of isolation techniques, chosen having regard to its physical and chemical properties. For example, any or all of the following isolation techniques may be employed: extraction of the liquor from the culture broth with a hydrophilic solvent (such as diethyl ether, ethyl acetate, chloroform or benzene); extraction of the organism with a hydrophilic solvent (such as acetone or an alcohol); concentration, e.g. by evaporating off some or part of the solvent under reduced pressure; dissolution into a more polar solvent (such as acetone or an alcohol); removal of impurities with a less polar solvent (such as petroleum ether or hexane); gel filtration through a column of a material such as Sephadex (a trade name for a material available from Pharmacia, Co. Limited, U.S.A.); absorptive chromatography with active carbon or silica gel; and other similar methods. By using a suitable combination of these techniques, the desired Monacolin K can be isolated from the culture broth as a pure substance.

The Monacolin K produced by the process of the present invention is characterized by the following properties:

1. Colour and form: Colourless needles.
2. Melting point: 157–158° C.
3. Elemental analysis: Found: C, 72.67%; H, 9.13%; O, 18.2%. Calculated: C, 71.25%; H, 8.97%; O, 19.78%.
4. Molecular weight: 404 (by mass spectrometry).
5. Molecular formula: $C_{24}H_{36}O_5$.
6. Ultraviolet absorption spectrum (methanol):
    maxima at 232, 238 and 246 $\mu$m.
7. Solubility:
    Readily soluble in methanol, ethanol, acetone, ethyl acetate, chloroform and carbon tetrachloride.
    Soluble in benzene.
    Insoluble in hexane and petroleum ether.
8. Colour reaction:
    Pink colour with 50% v/v sulphuric acid on a thin layer chromatograph on silica gel.
9. Thin layer chromatography:
    $R_f$ value =0.45 [silica gel $F_{254}$ (Merck & Co., Ltd.) 0.25 mm thick, multiple (×3) development with a 7:3 by volume mixture of methylene chloride and ethyl acetate and treated with iodine or 50% v/v sulphuric acid].

The compound is neutral and is insoluble in neutral or acidic aqueous media. It is, however, converted to an acidic substance by treatment with alkali and this acidic substance is soluble in water. The acidic substance can be extracted with ethyl acetate or chloroform at acid pH values and will revert to Monacolin K on evaporation of the solvent.

The physiological activity of Monacolin K can be assayed and determined quantitatively by the following in vivo and in vitro tests, which can be used to monitor the production of Monacolin K in the course of the process of the invention.

In vivo test with rabbits

In this test, the ability of Monacolin K to reduce cholesterol levels in rabbit blood is measured. The animals employed should each weigh from 2.5 to 3.0 kg. At the beginning of the tests, blood is collected from a vein in an ear of each rabbit and the cholesterol level in the blood serum is measured by a conventional method. A predetermined quantity of Monacolin K or of a Monacolin K-containing culture broth is then administered orally continuously for from 1 to 5 days and the cholesterol level in the blood serum is measured at stages after the administration. The potency of the Monacolin K or Monacolin K-containing culture medium can be determined quantitatively from the blood cholesterol levels obtained prior to and after administration of the Monacolin K.

In vitro test with rat liver

Crude enzymes from rat liver are reacted with radioactive acetic acid for 60 minutes at 37° C. Products biosynthesized is saponified, and the radioactive cholesterol is extracted and then precipitated with digitonin. The radioactivity is measured to determine the amount of cholesterol produced. The procedure is repeated, except that Monacolin K or a Monacolin K-containing culture broth is added at the beginning of the reaction, and the amount of cholesterol biosynthesized is again determined, thus giving a quantitative measurement of the inhibitory effect of Monacolin K [Bricker et al, The Journal of Biological Chemistry, 247, 4914 (1972)]. This test is particularly useful as a quick and easy way of monitoring Monacolin K production during the cultivation process of the present invention.

We have also demonstrated the ability of Monacolin K to lower the blood and liver cholesterol levels by various in vivo tests.

Reduction of blood and liver cholesterol levels in rats

The animals used were rats of the Wistar Imamichi strain, each having a body weight of about 300 g. The tests were conducted on groups of rats, each group consisting of 5 animals. Each animal was intravenously injected with 400 mg/kg of Triton WR-1339 (a trade name for a material known to increase the blood cholesterol level) whilst simultaneously administering 10 mg/kg of Monacolin K either orally or intraperitoneally. 20 hours after oral administration or 14 hours after intraperitoneal administration, the rats were sacrificed by bleeding and the blood and livers were collected and their cholesterol levels were determined by conventional means. As a result, it was established that blood cholesterol levels had been reduced, as compared with the control group of animals to which Triton WR-1339 alone had been administered, by 22.4% in the case of oral administration and 23.9% in the case of intraperitoneal administration. Liver cholesterol levels had been reduced by 16.7% in the animals to which Monacolin K had been administered orally.

Reduction of blood cholesterol levels in rabbits

The test animals used were rabbits having a body weight of from 2.7 kg to 2.9 kg. Each rabbit was given orally 1 mg/kg of Monacolin K twice each day (morning and evening) continuously for 5 days. Prior to administration and at 3 and 5 days after administration, blood was collected from a vein in the ear and the cholesterol levels in the blood serum were determined. As a result, it was found that the cholesterol levels at 3 and 5 days after administration of Monacolin K were 15% and 29%, respectively, lower than the level prior to administration of Monacolin K.

We have found that Monacolin K gives 50% inhibition of cholesterol biosynthesis at a concentration of 0.002 μg/ml by the test wherein acetic acid is reacted with enzyme from rat liver. We have found that Monacolin K inhibits HMG-CoA reductase, which is the rate-limiting enzyme in a competitive manner with respect to HMG-CoA. The ki value is $5.3 \times 10^{-10}$M. The Ki value is the inhibition constant and, specifically, is the dissociation constant of the enzyme-inhibitor complex. The value is obtained by the product of the concentrations of enzyme and of inhibitor divided by the concentration of the enzyme-inhibitor complex.

Not only does Monacolin K have a valuable inhibitory effect on the biosynthesis of cholesterol, but it also has a very low toxicity, making its use for the treatment of hypercholesteraemia potentially very attractive. Specifically the acute oral toxicity ($LD_{50}$) of Monacolin K in the mouse is 1 g/kg body weight or more.

The Monacolin K may be administered orally or parenterally in the form of a capsule, tablet, injectable preparation or any other known formulation, although we normally prefer to administer it orally. The dose will vary, depending upon the age and body weight of the patient and the severity of the condition, but, in general, the daily dose for an adult would be from 0.5 to 50 mg, either as a single dose or in 2 or 3 divided doses. However, in view of the low toxicity of the compound, higher doses may be employed if required.

The invention is further illustrated by the following non-limiting Examples.

EXAMPLE 1

300 liters of a culture medium having a pH of 7.4 before sterilisation and containing 1.5% w/v soluble starch, 1.5 w/v glycerine, 2% w/v fish meal and 0.2% w/v calcium carbonate were charged into a 600 liter fermenter and inoculated with the organism *Monascus ruber* SANK 18174 (FERM 4957). Cultivation of the organism was effected for 120 hours at 27° C. with an aeration rate of 300 liters per minute and agitation at 190 revolutions per minute. The culture broth was filtered in a filter press, giving 290 liters of filtrate and 60 kg (wet weight) of the organism.

The pH of the filtrate was adjusted to 4.0 by addition of 6 N hydrochloric acid and then the filtrate was extracted with 400 liters of ethyl acetate. This extract was concentrated, dried over anhydrous sodium sulphate and then evaporated to dryness to give 95 g of an oily product. The organism (having 2.5 times as much activity as the filtrate) was extracted twice, each time with 100 liters of 80% v/v aqueous methanol. The methanol was evaporated from the extract and the residue was extracted twice, each time with 100 liters of ethyl acetate. The combined extracts were concentrated, dried over anhydrous sodium sulphate and then evaporated to dryness to give 128 g of an oily product. This was combined with the residue from the filtrate of the culture broth.

The resulting 223 g of combined oily product were adsorbed in a column containing 3 kg of silica gel (Wakogel C-200) which had previously been treated with benzene. The column was eluted successively with 10 liters of benzene and then with 180 liters of a 4:1 by volume mixture of methylene chloride and ethyl acetate. The active fraction was evaporated to dryness to give 30 g of an oily product, which was then adsorbed in a column containing 450 g of silica gel (Wakogel C-200), which had previously been treated with hexane. The column was eluted successively with 2 liters of hexane, 30 liters of a 9:1 by volume mixture of hexane and acetone and 30 liters of a 4:1 by volume mixture of hexane and acetone. The active fraction was concentrated and the precipitate was filtered off. The filtrate was evaporated to dryness, giving 4 g of an oily product, which was adsorbed in a column containing 96 g of silica gel (Wakogel C-200), which had previously been treated with hexane. The column was eluted successively with 500 ml of hexane and 6 liters of a 9:1 by volume mixture of hexane and acetone. The active fraction was evaporated to dryness to give 521 mg of an oily product, which was adsorbed in a column containing 30 g of silica gel (Wakogel C-200), which had previously been treated with benzene. The column was eluted successively with 10 ml of benzene, 100 ml of a 95:5 by volume mixture of benzene and ethyl acetate and 900 ml of a 4:1 by volume mixture of benzene and ethyl acetate. The active fraction was concentrated to give 92 mg of colourless crystals which, on recrystallization from aqueous acetone, gave 54 mg of Monacolin K in the form of colourless needles.

EXAMPLES 2-8

300 liters of a culture medium having a pH of 6.0 before sterilization and containing 2% w/v glucose, 2% w/v peptone (Kyokuto brand, available from Kyokuto Seiyaku KK, Japan) and 0.3% w/v corn steep liquor were charged into a 600 liter fermenter and inoculated with one of the microorganisms listed in the following Table 1. Cultivation of the microorganism was continued for 96 hours at 27° C. with an aeration rate of 300 liters per minute and agitation at 190 revolutions per minute.

At the end of this time, 1 ml of the culture broth was then removed and extracted with ethyl acetate adjusted to a pH value of 3-4. The extract was then taken up in 0.2 ml of the reaction mixture described by M Kuroda, Y. Hazama-Shimada and A. Endo in Biochim. and Biophys. Acta., 486 (1977), pages 254-259 at 255 ("Inhibition of Sterol Synthesis by Citrinin in a Cell-free System from Rat Liver and Yeast") and A. Endo, M. Kuroda and Y. Tsujita in the Journal of Antibiotics, published by the Japanese Antibiotics Research Association, 29 No. 12 (December 1976), pages 1346-1348 and the percentage inhibition of cholesterol biosynthesis was determined. The results are reported in Table 1 as activity units of inhibition per ml of culture broth, 50% inhibition of cholesterol biosynthesis being equivalent to 1 unit/ml.

TABLE 1

| Ex. No. | Organism | Inhibition activity units/ml |
|---|---|---|
| 2 | *Monascus purpureus* SANK 10271 | 120 |
| 3 | *Monascus ruber* SANK 10671 | 120 |
| 4 | *Monascus vitreus* SANK 10960 | 150 |
| 5 | *Monascus paxii* SANK 11172 | 120 |
| 6 | *Monascus ruber* SANK 13778 | 440 |
| 7 | *Monascus ruber* SANK 15177 | 2,400 |
| 8 | *Monascus ruber* SANK 18174 | 20,000 |

These results demonstrate the production of very substantial quantities of Monacolin K by the microorganisms of the present invention.

EXAMPLE 9

The procedure described in Examples 2-8 was repeated, except that the microorganism used was *Monascus anka* SANK 10171 and the samples of the culture medium were removed after 96 hours, 168 hours, 216 hours, and 288 hours cultivation. The inhibition activity, measured by the same test as was used in Examples 2-8, was 110, 100, 30 and 80 units/ml, respectively.

EXAMPLES 10-17

300 liters of a liquid culture medium having a pH value of 5.5 before sterilization and containing 5% w/v glucose, 0.5% w/v corn steep liquor, 2% w/v peptone (Kyokuto) and 0.5% w/v ammonium chloride were charged into a 600 liter cultivation tank. One of the strains listed in Table 2 was then inoculated into the medium and cultivated for 120 hours. This was repeated separately for each of the other strains.

After cultivation, each medium was filtered through a filter press, giving a wet mycelial cake in the amount shown in Table 2 and a filtrate. The pH value of the filtrate was adjusted to 4.0 by the addition of 6 N hydrochloric acid, after which it was extracted with 400 liters of ethyl acetate. The extract, measuring about 400 liters, was then condensed by evaporation under reduced pressure and dried over anhydrous sodium sulphate. The condensed extract was further condensed and then evaporated to dryness, affording an oil in an amount shown in Table 2 as "amount of extract from liquor".

Meanwhile, the mycelial cake, which had about 2-3 times the activity of the corresponding filtrate, was extracted twice, each time with 100 liters of 80% v/v aqueous methanol. The extract was condensed and dried over anhydrous sodium sulphate. The condensed extract was further condensed and then evaporated to dryness, giving an oil in an amount shown in Table 2 as "amount of extract from mycelial cake".

The oils resulting from the respective filtrate and mycelial cake were combined and then adsorbed on a column of silica gel (3 kg of Wakogel C-200, prepared with benzene), which was eluted, in turn, with 10 liters of benzene and 180 liters of a 4:1 by volume mixture of methylene chloride and ethyl acetate. The active fraction from the elution was condensed and evaporated to dryness, giving an oil in the amount shown in Table 2 under "Fraction 1". This oil was adsorbed on a column containing 340 to 450 g of silica gel (Wakogel C-200, previously prepared with hexane), the amount of silica gel corresponding to 1 g per 65 mg of oil. The column was then eluted, in turn, with 1.5-2 liters of hexane, 23-30 liters of a 9:1 by volume mixture of hexane and acetone and 23-30 liters of a 4:1 by volume mixture of hexane and acetone.

The active fraction from this elution was condensed and the crystals which precipitated were filtered off. The resulting residue was further condensed and then evaporated to dryness, giving an oil in the amount shown in Table 2 under "Fraction 2". This fraction was adsorbed on a column containing 18-135 g of silica gel (Wakogel C-200, previously prepared with hexane), the amount of silica gel corresponding to 1 g per 42 mg of oil. The column was then eluted, in turn, with 100-750 ml of hexane and 1.2-9 liters of a 9:1 by volume mixture of hexane and acetone. The active fraction from this elution was condensed and evaporated to dryness, giving an oil in the amount shown in Table 2 under "Fraction 3". This oil was adsorbed on a column containing 6-45 g of silica gel (Wakogel C-200, previously prepared with benzene), the amount of silica gel corresponding to 1 g per 17 mg of oil. The column was then eluted, in turn, with 15-100 ml of benzene, 15-100 ml of a 95:5 by volume mixture of benzene and ethyl acetate and 120–1,200 ml of a 4:1 by volume mixture of benzene and ethyl acetate. The active fraction was condensed, giving crude crystals of Monacolin K in the amount shown in Table 2. These crude crystals were recrystallized from aqueous acetone, giving recrystallized crystals in the form of colourless needles in the amount shown in Table 2.

TABLE 2

| Ex. No. | Strain | Amount of mycelial cake (kg) | Amount of extract from liquor (g) | Amount of extract from mycelial cake (g) | Amount of combined extract (g) |
|---|---|---|---|---|---|
| 10 | Monascus anka SANK 10171 | 56 | 86 | 116 | 202 |
| 11 | Monascus purpureus SANK 10271 | 55 | 87 | 114 | 201 |
| 12 | Monascus ruber SANK 10671 | 55 | 88 | 115 | 203 |
| 13 | Monascus vitreus SANK 10960 | 61 | 89 | 123 | 212 |
| 14 | Monascus paxii SANK 11172 | 58 | 91 | 120 | 211 |
| 15 | Monascus ruber SANK 13778 | 63 | 95 | 127 | 222 |
| 16 | Monascus ruber SANK 15177 | 58 | 91 | 119 | 210 |
| 17 | Monascus ruber SANK 18174 | 62 | 93 | 125 | 218 |

| Ex. No. | Fraction 1 (g) | Fraction 2 (g) | Fraction 3 (mg) | Monacolin K Crude crystals (mg) | Monacolin K Recrystallized crystals (mg) |
|---|---|---|---|---|---|
| 10 | 22 | 0.9 | 102 | 9.3 | 0.8 |
| 11 | 23 | 1.3 | 113 | 10.4 | 1.1 |
| 12 | 22 | 0.75 | 98 | 8.9 | 0.8 |
| 13 | 25 | 1.1 | 110 | 10.7 | 1.2 |
| 14 | 24 | 2.2 | 121 | 12.0 | 1.6 |
| 15 | 28 | 1.65 | 216 | 14.2 | 6.3 |
| 16 | 26 | 1.8 | 235 | 24.4 | 9.8 |
| 17 | 29 | 5.7 | 765 | 135.0 | 81.0 |

We claim:

1. A process for preparing Monacolin K comprising cultivating at least one strain of the genus Monascus, selected from the group consisting of *Monascus anka* SANK 10171 (IFO 6540), *Monascus purpureus* SANK 10271 (IFO 4513), *Monascus ruber* SANK 10671 (FERM 4958), *Monascus vitreus* SANK 10960 (FERM 4960), *Monascus paxii* SANK 11172 (IFO 8201), *Monascus ruber* SANK 13778 (FERM 4959), *Monascus ruber* SANK 15177 (FERM 4956) and *Monascus ruber* SANK 18174 (FERM 4957), in a culture medium containing an assimilable carbon source and an assimilable nitrogen source to produce Monacolin K and isolating Monacolin K from the culture medium.

2. The process of claim 1 wherein said cultivation is carried out at a temperature of from 7° to 40° C.

3. The process of claim 1 wherein said cultivation is carried out at a temperature of from 20° to 30° C.

4. The process of claim 2 wherein said assimilable carbon source is at least one selected from the group consisting of glucose, glycerine and starch.

5. The process of claim 2 or 4 wherein said assimilable nitrogen source is at least one selected from the group consisting of peptone, corn steep liquor and ammonium chloride.

6. The process of claim 1 wherein said assimilable carbon source is at least one selected from glucose, glycerine and starch and wherein said assimilable nitrogen source is at least one selected from peptone, corn steep liquor and ammonium chloride.

7. The process of claim 3 wherein said assimilable carbon source is at least one selected from glucose, glycerine and starch and wherein said assimilable nitrogen source is at least one selected from peptone, corn steep liquor and ammonium chloride.

8. The process of any one claims 2, 4, 6 or 7 wherein said strain is *Monascus ruber* SANK 15177 (FERM 4956).

9. The process of claim 8 wherein said cultivation is carried out at a temperature of from 23° C. to 30° C.

10. The process of anyone of claims 2, 3, 4, 6 or 7 wherein said strain is *Monascus ruber* SANK 10671 (FERM 4958).

11. The process of anyone of claims 2, 3, 4, 6 or 7 wherein said strain is *Monascus ruber* SANK 13778 (FERM) 4959.

12. The process of anyone of claims 2, 3, 4, 6 or 7 wherein said strain is *Monascus ruber* SANK 18174 (FERM) 4957.

* * * * *